US011305072B2

(12) United States Patent
Murray et al.

(10) Patent No.: US 11,305,072 B2
(45) Date of Patent: Apr. 19, 2022

(54) TAMPER EVIDENT ASSEMBLY FOR SYRINGES

(71) Applicant: Fresenius Kabi USA, LLC, Lake Zurich, IL (US)

(72) Inventors: Christopher J. Murray, Chicago, IL (US); Anthony Ferraro, Vernon Hills, IL (US); Gang Ju, Vernon Hills, IL (US); Robert Speek, Highland Park, IL (US)

(73) Assignee: FRESENIUS KABI USA, LLC, Lake Zurich, IL (US)

( * ) Notice: Subject to any disclaimer, the term of this patent is extended or adjusted under 35 U.S.C. 154(b) by 413 days.

(21) Appl. No.: 16/408,947

(22) Filed: May 10, 2019

(65) Prior Publication Data

US 2020/0164161 A1 May 28, 2020

Related U.S. Application Data

(60) Provisional application No. 62/772,461, filed on Nov. 28, 2018.

(51) Int. Cl.
*A61M 5/00* (2006.01)
*A61M 5/50* (2006.01)
*A61M 5/31* (2006.01)
*A61J 1/20* (2006.01)
*B65B 3/00* (2006.01)
*A61M 5/32* (2006.01)

(52) U.S. Cl.
CPC ......... *A61M 5/5086* (2013.01); *A61J 1/2096* (2013.01); *A61M 5/3134* (2013.01); *B65B 3/003* (2013.01); *A61M 5/3202* (2013.01); *A61M 2005/312* (2013.01); *A61M 2005/3104* (2013.01); *A61M 2205/584* (2013.01)

(58) Field of Classification Search
CPC combination set(s) only.
See application file for complete search history.

(56) References Cited

U.S. PATENT DOCUMENTS 4,174,238 A 11/1979 Fowles et al.
4,667,837 A 5/1987 Vitello et al.
5,135,496 A 8/1992 Vetter et al.
(Continued)

FOREIGN PATENT DOCUMENTS

EP 0716860 A2 6/1996
EP 0766975 A1 4/1997
(Continued)

OTHER PUBLICATIONS

International Patent Application No. PCT/US2019/063283; Int'l Search Report and the Written Opinion; dated Apr. 2, 2020; 28 pages.

*Primary Examiner* — Rebecca E Eisenberg
(74) *Attorney, Agent, or Firm* — BakerHostetler (57) ABSTRACT

The present disclosure describes a syringe assembly including a syringe including a Luer connection and a tip, a plunger, a tip cap, a tamper evident cap disposed over the tip cap, and a film including a frangible connection. The film secures the tamper evident cap to the Luer connection, where the frangible connection can break under a force applied to the tamper evident cap such that the tamper evident cap disengages from the Luer connection when the frangible connection breaks.

25 Claims, 6 Drawing Sheets

(56) References Cited

U.S. PATENT DOCUMENTS

| | | |
|---|---|---|
| 5,322,515 A | 6/1994 | Karas et al. |
| 5,328,474 A | 7/1994 | Raines |
| 5,554,134 A | 9/1996 | Bonnichsen |
| 5,624,402 A * | 4/1997 | Imbert ................. A61M 5/3134 604/111 |
| 5,649,622 A | 7/1997 | Hollister |
| 5,680,945 A | 10/1997 | Sander et al. |
| 5,785,691 A | 7/1998 | Vetter et al. |
| 5,833,653 A | 11/1998 | Vetter et al. |
| 5,851,200 A | 12/1998 | Higashikawa et al. |
| 5,944,699 A | 8/1999 | Barrelle et al. |
| 5,989,227 A | 11/1999 | Vetter et al. |
| 6,193,688 B1 | 2/2001 | Balestracci et al. |
| 6,196,998 B1 | 3/2001 | Jansen et al. |
| 6,330,959 B1 | 12/2001 | Dark |
| 6,432,088 B1 | 8/2002 | Huang et al. |
| 6,485,460 B2 | 11/2002 | Eakins et al. |
| 6,491,665 B1 | 12/2002 | Vetter et al. |
| 6,520,935 B1 | 2/2003 | Jansen et al. |
| 6,585,691 B1 | 7/2003 | Vitello |
| 6,726,652 B2 | 4/2004 | Eakins et al. |
| 6,846,303 B2 | 1/2005 | Eakins et al. |
| 6,942,643 B2 | 9/2005 | Eakins et al. |
| 7,144,238 B2 | 12/2006 | Chao |
| 7,374,555 B2 | 5/2008 | Heinz et al. |
| 7,488,307 B2 | 2/2009 | Rimlinger et al. |
| 7,632,244 B2 | 12/2009 | Buehler et al. |
| 7,806,861 B2 | 10/2010 | Witowski |
| 8,075,535 B2 | 12/2011 | Carrel et al. |
| 8,348,895 B1 | 1/2013 | Vitello |
| 8,353,869 B2 | 1/2013 | Ranalletta et al. |
| 8,591,462 B1 | 11/2013 | Vitello |
| 8,784,377 B2 | 7/2014 | Ranalletta et al. |
| 9,174,010 B2 | 11/2015 | Vedrine |
| 9,480,801 B2 | 11/2016 | Schiller et al. |
| 9,579,463 B2 * | 2/2017 | Okihara ................. A61M 5/28 |
| 9,731,082 B2 | 8/2017 | Vernizeau et al. |
| 9,758,281 B2 | 9/2017 | Glaser et al. |
| 9,821,152 B1 | 11/2017 | Vitello et al. |
| 9,925,340 B2 | 3/2018 | Glocker |
| 9,937,301 B2 | 4/2018 | Ward |
| 10,039,887 B2 | 8/2018 | Sundquist et al. |
| 10,124,122 B2 | 11/2018 | Zenker |
| 2001/0003150 A1 | 6/2001 | Imbert |
| 2003/0014018 A1 | 1/2003 | Giambattista et al. |
| 2004/0133169 A1 | 7/2004 | Heinz et al. |
| 2004/0225258 A1 | 11/2004 | Balestracci |
| 2008/0300550 A1 | 12/2008 | Schiller et al. |
| 2009/0283493 A1 | 11/2009 | Witowski |
| 2011/0015578 A1 | 1/2011 | Lowke |
| 2012/0029438 A1 * | 2/2012 | Vernizeau ............. A61M 5/344 604/189 |
| 2012/0111368 A1 | 5/2012 | Rahimy et al. |
| 2013/0338604 A1 | 12/2013 | Roedle |
| 2014/0262883 A1 | 9/2014 | Devouassoux et al. |
| 2015/2046185 | 9/2015 | Heinz |
| 2015/0343155 A1 | 12/2015 | Zenker et al. |
| 2016/0001015 A1 | 1/2016 | Kucuk et al. |
| 2016/0151584 A1 | 6/2016 | Deleuil et al. |
| 2016/0200484 A1 | 7/2016 | Cosman |
| 2018/0273261 A1 | 9/2018 | Qiu |
| 2019/0099557 A1 | 4/2019 | Potdar et al. |
| 2019/0161229 A1 | 5/2019 | Mase |

FOREIGN PATENT DOCUMENTS

| | | |
|---|---|---|
| EP | 1410819 A1 | 4/2004 |
| EP | 2826508 A1 | 1/2015 |
| EP | 2900301 A1 | 8/2015 |
| EP | 3381492 A1 | 10/2018 |
| JP | 2002315827 A * | 10/2002 |
| WO | 2014049097 A1 | 4/2014 |
| WO | 2018024624 A1 | 2/2018 |

* cited by examiner

TAMPER EVIDENT ASSEMBLY FOR SYRINGES

CROSS REFERENCE TO RELATED APPLICATIONS

This application claims the benefit of U.S. Provisional Patent App. No. 62/772,461, filed Nov. 28, 2018, the disclosure of which is hereby incorporated by reference herein.

TECHNICAL FIELD

The present disclosure generally relates to tamper detection devices, and, more particularly, to a tamper evident cap and film for detecting tampering of syringes filled with a material.

BACKGROUND

Syringe assemblies are used to hold, transport, and deliver materials. For example, syringes are often utilized in medical environments to administer one or more medicinal materials. Syringe assemblies may differ in size, and their specific dimensions are dictated by the desired application and the specific material to be administered. In some instances, syringes may be pre-filled with one or more materials that are then dispensed from the syringe and combined with other elements.

Many industrial applications require mechanisms that prevent tampering with a particular product. This is especially the case with syringes used in the medical profession, where it is important for medical staff and patients to be aware of any tampering with the syringe or the material contained therein. Existing technology for detecting and preventing tampering is often cumbersome, difficult to use, increases risks of injury to the user, and increases the likelihood of contaminating the patient or the medical environment. Further, the addition of a tampering device can often require changes to be made to the manufacturing process of a syringe or its constituent components, which increases associated production costs and complexity of manufacturing.

Therefore, there is a need for tamper evident assembly configured to be used with syringes having preexisting designs that are filled with a material.

SUMMARY

An embodiment of the present disclosure is syringe assembly comprising a syringe having a barrel body that extends from a proximal end to a distal end and defines a chamber extending along an axial direction therethrough, a Luer connection at the distal end, and a tip extending from the distal end along the axial direction and defining an outlet in fluid communication with the chamber, where the chamber contains a material. The syringe assembly also includes a plunger received within the chamber of the syringe to create a fluid seal within the barrel body, a tip cap defining a central passage configured to receive a portion of the tip such that the tip cap creates a fluid seal over the outlet, and a tamper evident assembly. The tamper evident assembly includes a tamper evident cap disposed over the tip cap, where the tamper evident cap has a main body that defines a proximal end defining an opening, a distal end opposite the proximal end along the axial direction, an outer surface, and an inner surface opposite the outer surface that defines a passage configured to receive the tip cap. The tamper evident assembly further includes a film including a frangible connection and configured to secure the tamper evident cap to the Luer connection, where the frangible connection is configured to break under a force applied to the tamper evident cap such that the tamper evident cap is configured to disengage from the Luer connection when the frangible connection breaks.

Another embodiment of the present disclosure is a method of filling a syringe with a material, the method comprising receiving a syringe having a barrel body extending from a distal end having a Luer connection and a tip, where the tip defines an outlet having a tip cap placed thereon, to an open proximal end, the barrel body defining a chamber that extends along an axial direction therethrough, and filling the chamber with the material through the open proximal end. The method also include placing plunger at the proximal end of the chamber, placing a tamper evident cap over the tip cap, attaching a film to the tamper evident cap and the Luer connection such that the film secures the tamper evident cap to the Luer connection.

Another embodiment of the present disclosure is a tamper evident assembly that includes a tamper evident cap and a film. The tamper evident cap has a main body that defines a proximal end defining an opening, a distal end opposite the proximal end along the axial direction, an outer surface, and an inner surface opposite the outer surface that defines a passage configured to receive a tip cap and a Luer connection of a syringe. The film is configured to secure the tamper evident cap to the Luer connection. The film includes a frangible connection which is configured to break under a force applied to the tamper evident cap, such that the tamper evident cap is configured to disengage from the Luer connection when the frangible connection breaks.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In the drawings.

DETAILED DESCRIPTION OF ILLUSTRATIVE EMBODIMENTS

Described herein is a syringe assembly 10 that includes a tamper evident assembly 180 including a tamper evident cap 200 and a film 250. Certain terminology is used to describe the syringe assembly 10 in the following description for convenience only and is not limiting. The words "right," "left," "lower," "upper," "lower," "proximal," and "distal" designate directions in the drawings to which reference is made. The words "inner" and "outer" refer to directions toward and away from, respectively, the geometric center of the description to describe the syringe assembly 10 and related parts thereof. The words "axially" and "radially" refer to directions along the orthogonal axial and radial directions A, R, respectively. The terminology includes the above-listed words, derivatives thereof and words of similar import.

Referring to FIGS. 1-4, the syringe assembly 10 includes a syringe 100 having a barrel body 103. The barrel body 103 can extend from a proximal end 100a to a distal end 100b along the axial direction A. The barrel body 103 can be molded from glass in one embodiment, though other materials are contemplated. For example, the barrel body 103 can be molded from cyclic olefin copolymer (COC), cyclic olefin polymer (COP), or various other plastic materials. In one embodiment, the barrel body 103 can comprise a substantially transparent material, such that a user of the syringe assembly 10 can monitor the material levels within the barrel body 103, though barrel bodies 103 having various levels of opacity are contemplated. The barrel body 103 is depicted as comprising a substantially cylindrical shape, though the present disclosure is not intended to be limited as such. The barrel body 103 can have an outer surface 103a that extends from the proximal end 100a to the distal end 100b along the axial direction A, an inner surface 103b opposite the outer surface 103a that also extends from the proximal end 100a to the distal end 100b along the axial direction A, and a distal surface 103c that extends substantially along the radial direction R at the distal end 100b of the barrel body 103. The inner surface 103b of the barrel body 103 defines a chamber 109 that extends along the axial direction A from an opening 106 at the proximal end 100a to the tip 126 at the distal end 100b. The chamber 109 is configured to receive and store a material, such as a liquid, for dispensing through the tip 126. The syringe assembly 10 further includes a Luer connection 140 at the distal end 100b of the barrel body 103, where the Luer connection 140 will be discussed further below. The syringe 100 also includes a flange 112 extending radially outwards from the proximal end 100a of the barrel body 103, where the function of the flange 112 will be described further below. Though depicted as defining an oval shape with two flat, oppositely positioned sides, the flange 112 can define other shapes as desired.

The chamber 109 can be sized and configured to receive a plunger 50, such that the plunger 50 is capable of sliding along the axial direction A through the chamber 109. The plunger 50 can have a substantially cylindrical body 53, though the shape of the body 53 will generally conform to the shape of the chamber 109. The body 53 can be comprised of a substantially flexible material such as rubber, though other embodiments are contemplated where the plunger 50 comprises other materials. The plunger 50 can further include a plurality of ridges 56 extending radially outwards from the body 53. As shown, the plurality of ridges 56 extend substantially circumferentially around the body 53 and are aligned and spaced apart along the axial direction A. However, the ridges 56 can comprise different sizes, shapes, and arrangements in other embodiments. The ridges 56 can function to engage the inner surface 103b of the barrel body 103 of the syringe so as to create a fluid seal between the plunger 50 and the syringe 100. As the plunger 50 moves distally through the chamber 109, the plunger 50 can function to push material out of the chamber 109 through the tip 126. Alternatively, as the plunger 50 moves proximally through the chamber 109, the plunger 50 can function to draw material into the chamber 109 through the tip 126.

The plunger 50 can define a bore that extends into the body 53 from its proximal end. The bore can be configured to engage a plunger rod 25 by any suitable means, e.g., screw fit, simple interference fit, snap-fit, or barbed engagement. The plunger rod 25 extends from a proximal end 25a to a distal end 25b opposite the proximal end 25a along the axial direction A. The plunger rod 25 can comprise a rod body 28 at its center, where the rod body 28 comprises an elongated, axially-extending rod. Connected to the rod body 28, the plunger rod 25 can include a plurality of walls 31 extending radially outwards from the rod body 28. As depicted, each of the walls 31 comprises multiple sections that each extend from the rod body 28 by various distances. However, other embodiments of the wall 31 are contemplated. For example, each of the walls 31 can define a substantially rectangular body that extends radially outwards from the rod body 28 and axially along the length of the rod body 28. The plunger rod 25 is shown as including four walls 31, where the walls 31 are arranged about the rod body 28 circumferentially spaced apart 90 degrees, such that the arrangement of walls 31 forms a substantially plus-shaped orientation. However, the plunger rod 25 can include more or less walls 31 in other embodiments, and thus other arrangements of walls 31 can define other shapes. Additionally, it is contemplated that the walls 31 can define other shapes or extend to different extents along the axial length of the rod body 28 or radially outwards from the rod body 28. The walls 31 can function to provide stability and strength to the plunger rod 25, while minimizing the cross-sectional footprint of the plunger rod 25 so as to reduce material requirements for the plunger rod 25, thus reducing overall weight of the syringe assembly 10.

Once the plunger 50 and the distal end 25b of the plunger rod 25 are inserted into the chamber 109 of the syringe 100, and the proximal end 25a of the plunger rod 25 is located outside the chamber 109, the plunger rod 25 can be used to control dispensing of the material from within the chamber 109. In operation, movement of the plunger rod 25, and thus the plunger 50, distally through the chamber 109 along the axial direction A forces material to flow out of the chamber 109 through the tip 126. To do this, a user can, using one hand, pull the flange 112 of the syringe 100 and a flange 37 of the plunger rod 25 towards each other. Conversely, movement of the plunger rod 25, and thus the plunger 50, proximally through the chamber 109 along the axial direction A draws material into the chamber 109 through the tip 126. To do this, a user can, using one or two hands, push the flange 112 of the syringe 100 and the flange 37 of the plunger rod 25 away from each other.

Figure 1:
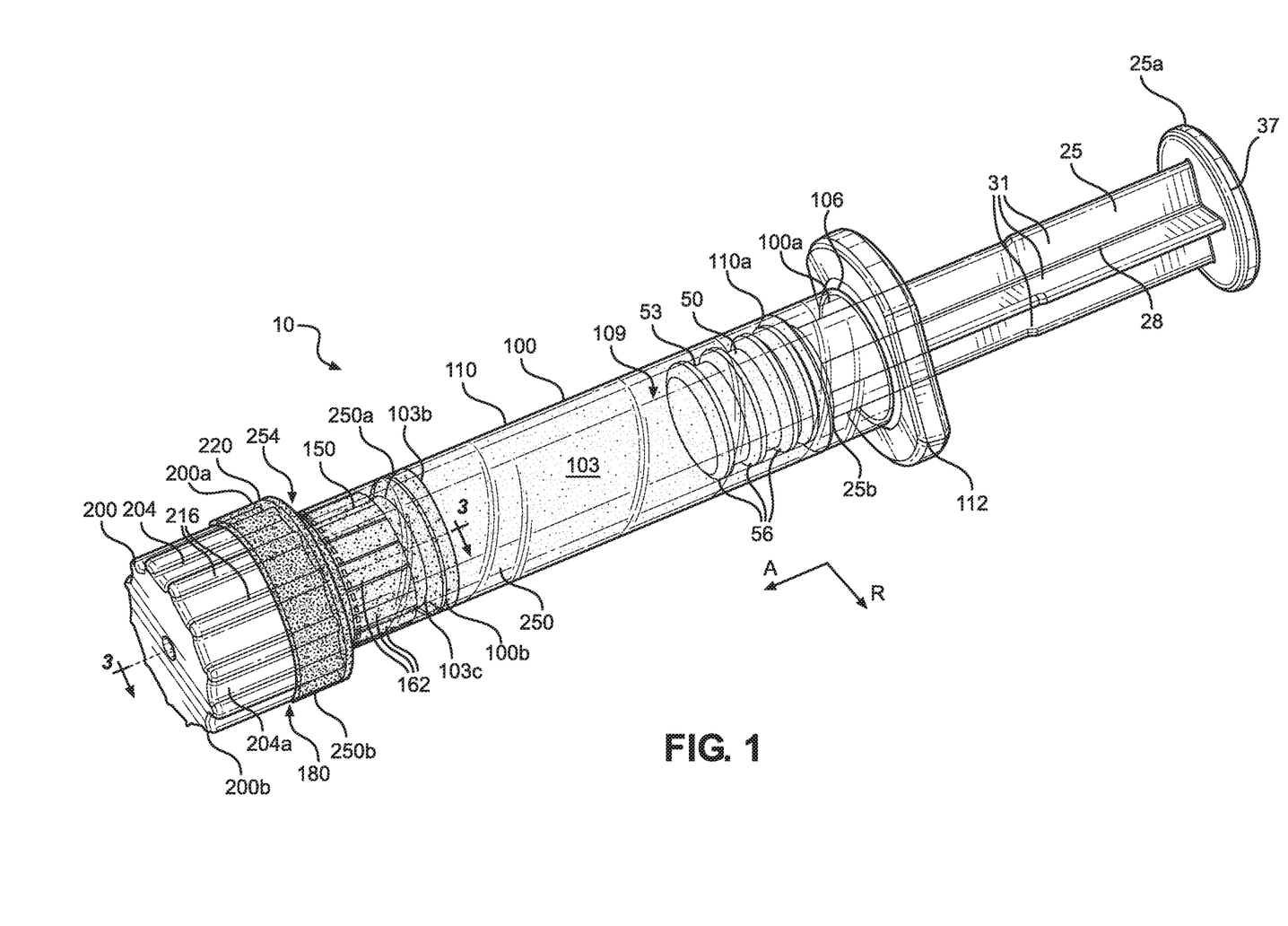
FIG. 1 illustrates a perspective view of a syringe assembly in accordance with an embodiment of the present disclosure.
Figure 2:
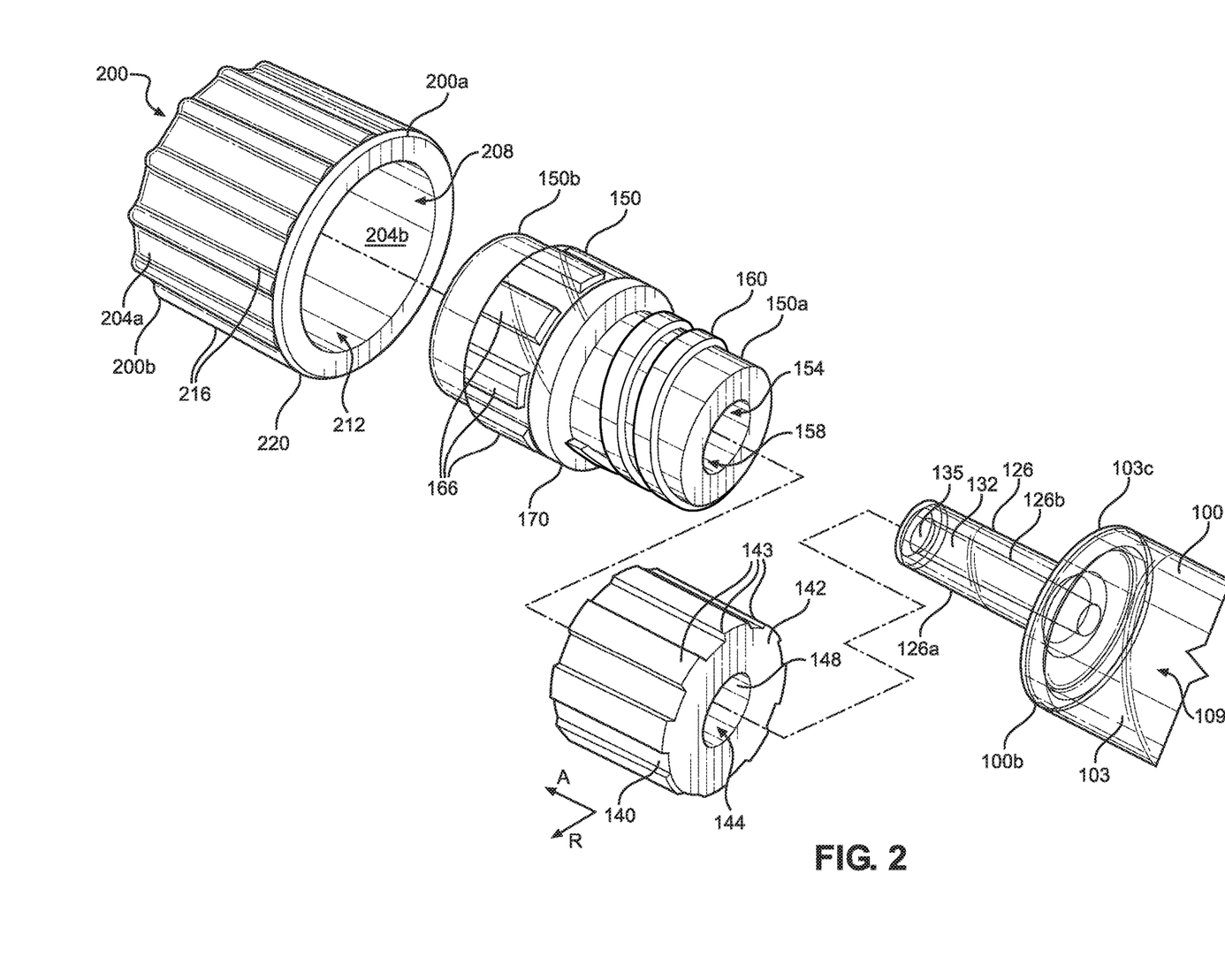
FIG. 2 illustrates an exploded view of a distal portion of the syringe assembly shown in FIG. 1.

Now referring to FIGS. 2-3, a Luer connection 140 of the syringe assembly 10 will be described in greater detail. In some embodiments, the Luer connection 140 is a separate component that is configured to be assembled onto a syringe 100, such as over the tip 126 of the syringe 100. The Luer connection 140 can comprise a ring 142 that is made of a material flexible enough to allow for radially expansion in the outward direction under pressure exerted on an inner wall 144 of the ring 142 when the central opening 148 of the Luer connection 140 is placed over the tip 126 of the syringe 100. The Luer connection 140 can include a plurality of ribs 143 that can extend radially outwards from the outer surface of the Luer connection 140. The ribs 143 can be arranged circumferentially around the Luer connection 140 so as to provide a texture that allows a label 110 and/or a film 250 to more easily engage the Luer connection 140, as will be described further below. Though one embodiment of the ribs 143 is shown, the present disclosure is not intended to be limited to such. In other embodiments, the outer surface of the Luer connection 140 is substantially smooth, i.e., lacking any ribs. In some embodiments, the inner surface of the Luer connection 140 comprises internal threads 149 configured to be engaged with outer threads 160 of a tip cap 150. In other embodiments, the inner surface of the Luer connection 140 is smooth.

In other embodiments, the Luer connection 140 is formed as an integral portion of the syringe 100, e.g., during a molding process. In such embodiments, the Luer connection 140 can extend from the distal end 100b of a syringe barrel body 103 along the axial direction A. At the center of the Luer connection 140 is included the tip 126 that that extends from the distal end 100b of the syringe barrel body 103 along the axial direction A. The tip 126 has an outer surface 126a and an inner surface 126b opposite the outer surface 126a, where the inner surface 126b defines a passage 132 that extends through the tip 126 to an outlet 135 of the tip 126. As the passage 132 and the outlet 135 are in fluid communication with the chamber 109 of the syringe 100, the passage 132 and the outlet 135 thus define the pathway for material being dispensed from the chamber 109 of the syringe 100.

Figure 3:
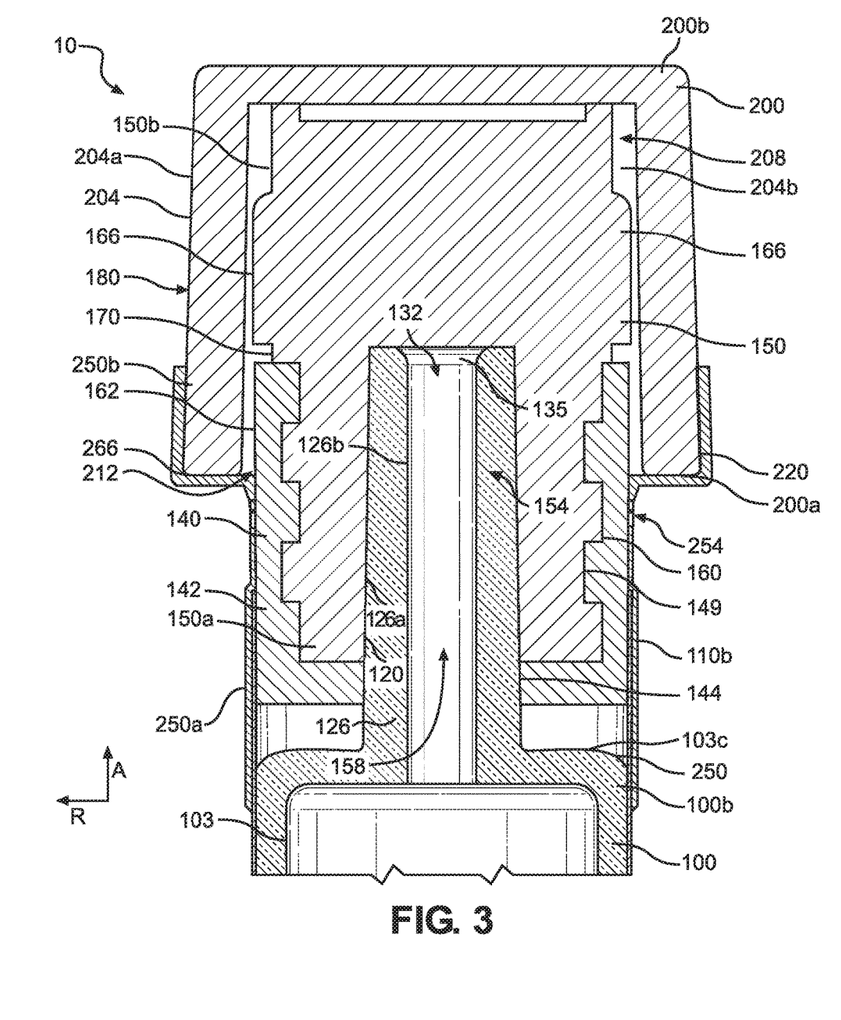
FIG. 3 illustrates a cross-sectional view of a distal portion of the syringe assembly shown in FIG. 1, taken along line 3-3 shown in FIG. 1.
Figure 4:
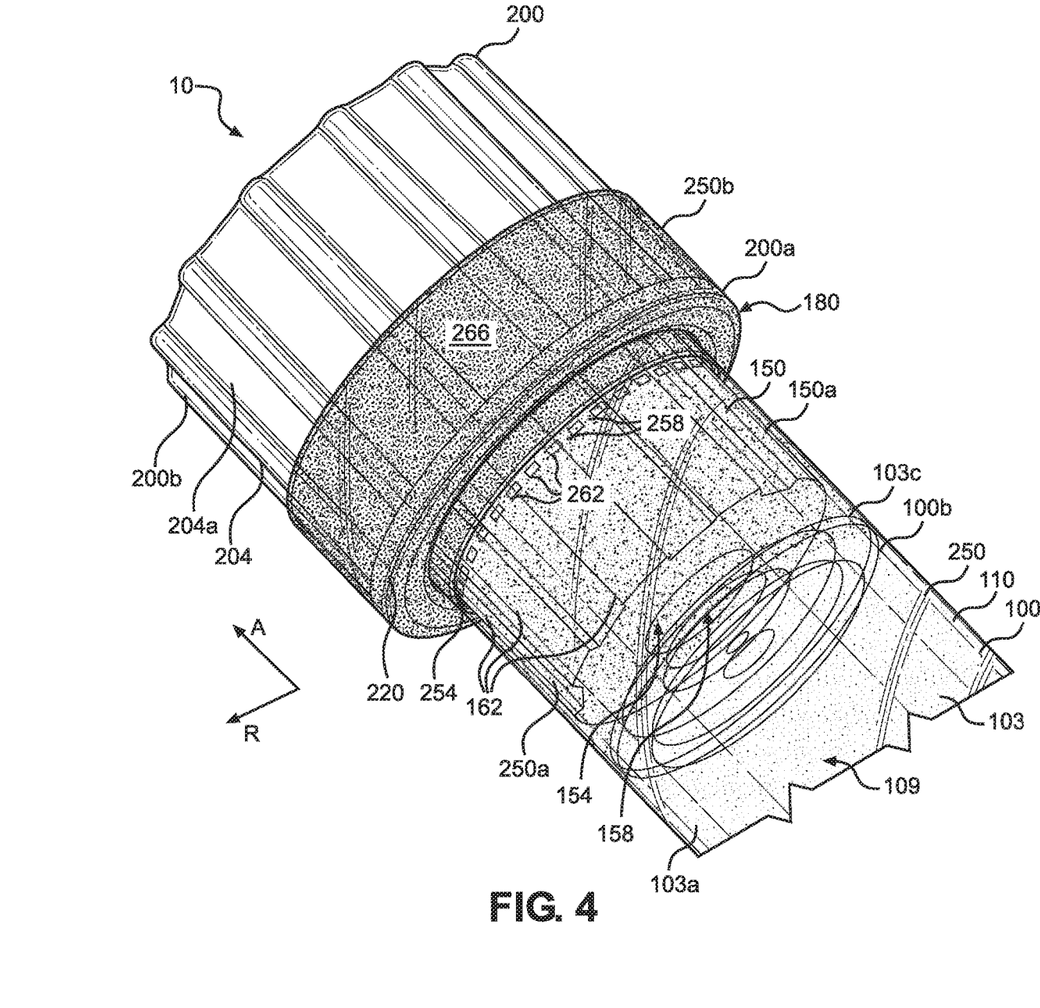
FIG. 4 illustrates a perspective view of the distal portion of the syringe assembly shown in FIG. 1.

In some embodiments, as depicted in FIG. 3, the assembly further comprises a label 110. In certain embodiments, the label 110 is continuous from a proximal end 110a to a distal end 110b opposite the proximal end 110a over at least a portion of the outer surface 103a of the syringe 100 and until at least a portion of the outer surface of the Luer connection 140. In other embodiments, the label 110 is continuous over at least a portion of the outer surface 103a of the syringe 100, the entire length of the outer surface of the Luer connection 140, and at least a portion of the outer surface of the tip cap 150. In such embodiments, the label 110 can be provided with an annular frangible connection, which must be broken in order to remove the tip cap 150 from the Luer connection 140. In some embodiments, as depicted in FIG. 3, a portion of the label 110 is imprisoned between a film 250 and the syringe 100 and/or between the film 250 and the Luer connection 140.

The label 110 can be attached to the syringe 100 and the Luer connection 140 (and, optionally, tip cap 150) by any suitable means. In some embodiments, the label 110 comprises a thermoplastic material and is attached to the syringe 100 and/or Luer connection 140 by heat-activated shrink wrapping. In certain embodiments, the label 110 comprises an adhesive and is attached to the syringe 100 and/or Luer connection 140 by applying pressure. In other embodiments, the label 110 is attached to the syringe 100 and/or Luer connection 140 by a combination of heat-activated shrink wrapping and an adhesive. In certain embodiments, the label 110 maintains the Luer connection 140 blocked in rotation and in translation with respect to the syringe 100 when the label 110 is attached. A preferred arrangement of a syringe 100, Luer connection 140, tip cap 150, and label 110 is described in U.S. Pat. No. 9,731,082, the contents of which are hereby incorporated by reference in its entirety.

The label 110 can be printed with information relating to the material contained within the chamber 109 of the syringe 100, e.g., active ingredient name, brand name, active ingredient concentration, volume, manufacturer, lot number, etc. The label 110 can also be bar coded with any combination of this information. The label 110 can be comprised of any suitable material, such as a thermoplastic material, paper, or a combination thereof. Thermoplastic materials that are suitable for a label 110 include, but are not limited to, polyvinyl chloride (PVC), polyethylene terephthalate (PET), oriented polystyrene (OPS), oriented polypropylene (OPP), polylactic acid (PLA) and mixtures thereof.

Continuing with FIGS. 1-4, the tip 126 extends from the distal end 100b of the barrel body 103 along the axial direction A. As depicted, the tip 126 can take the form of a substantially hollow tube, though other embodiments of the tip 126 are contemplated. The tip 126 can slightly taper inwards as it extends axially away from the distal surface 103c, or can alternatively define a substantially constant diameter. The tip 126 can have an outer surface 126a and an inner surface 126b that defines a passage 132 that extends through the tip 126. The passage 132 can extend from the chamber 109 of the syringe 100 to an outlet 135 of the tip 126. As the passage 132 and the outlet 135 are in fluid communication with the chamber 109, the passage 132 and the outlet 135 thus define a pathway for material being dispensed from the chamber 109 of the syringe 100. The passage 132 can take the form of a cylinder, a tapered tube, a stepped design, or any other suitable shape as desired.

After the syringe 100 has been filled, the outlet 135 needs to be sealed so as to prevent material from leaking out of the chamber 109. To do this, a tip cap 150 can be attached to the Luer connection 140 so as to seal the outlet 135. The tip cap 150 can extend from a proximal end 150a to a distal end 150b opposite the proximal end 150a along the axial direction A. As depicted, the proximal end 150a defines an opening 158, whereas the distal end 150b is closed. The tip cap 150 can define a central passage 154 extending along the axial direction A into the tip cap 150 from the opening 158. The tip cap 150 can further define a ridge 170 extending radially outwards from the outer surface of the tip cap 150, and substantially continuously around the entirety of the perimeter of the tip cap 150. In operation, the ridge 170 of the tip cap 150 abuts the distal end of the Luer connection 140 when the tip cap 150 has sealed the outlet 135. However, in other embodiments, the ridge 170 may only extend partially around the perimeter of the tip cap 150, or may not be present at all. Further, a plurality of ribs 166 can extend radially outwards from the outer surface of the tip cap 150 distal to the ridge 170. The ribs 166 can be arranged circumferentially around the tip cap 150 so as to provide a texture for grasping the tip cap 150 by a user of the syringe assembly 10. Though one embodiment of the ribs 166 is shown, the present disclosure is not intended to be limited to such.

In operation, the tip cap 150 is configured to be attached to the tip 126 of the syringe 100 so as to create a fluid seal over the outlet 135. To accomplish this, after the syringe 100 has been filled during assembly, the tip cap 150 can be screwed onto the Luer connection 140 such that the outer threads 160 of the tip cap 150 engage the internal threads 149 of the Luer connection 140. Alternatively, the tip cap 150 can be pushed into the Luer connection 140 with a force along the axial direction A, such that the tip cap 150 can be secured to the Luer connection 140 through an interference fit. When this is done, the tip 126 can be received within the central passage 154 of the tip cap 150 and continue to be disposed further through the central passage 154 until the tip 126 contacts the distal-most surface of the central passage 154, which indicates to the user that the tip cap 150 is completely secured to the syringe 100. At this point, the outlet 135 of the tip 126 can be disposed at the distal-most location in the central passage 154, thus creating a fluid seal over the tip 126. The ridge 170 can contact the upper surface of the outer wall of the Luer connection 140 so as to limit the extent to which the tip 126 can be disposed in the central passage 154. Once disposed into the Luer connection 140, the outlet 135 can be located at a distal-most part of the central passage 154 and the tip 126 can engage the inner surface of the tip cap 150, thus creating a fluid seal over the outlet 135.

Now referring to FIGS. 1-4, the tamper evident assembly 180 of the syringe assembly 10 will be discussed in detail. The tamper evident assembly 180 can include a tamper evident cap 200 and a film 250. The tamper evident cap 200 can include a main body 204 that extends from a proximal end 200a to a distal end 200b opposite the proximal end 200a along the axial direction A. The main body 204 can be configured as a substantially hollow cylinder, through other shapes are contemplated, as the shape of the tamper evident cap 200 can vary according to the shape of the syringe 100 and/or tip cap 150 of the particular syringe assembly 10 of which it is a part. The tamper evident cap 200 can be formed through injection molding, and can comprise a plastic such as medical grade polypropylene, polycarbonate, or polyethylene terephthalate. However, other methods of forming the tamper evident cap 200 and other materials for forming the tamper evident cap 200 are contemplated. The main body 204 defines an outer surface 204a and an inner surface 204b opposite the outer surface 204a, where the inner surface 204b defines a passage 208 configured to receive the Luer connection 140 and the tip cap 150. The distal end 200b of the main body 204 can be closed, whereas the proximal end 200a can define an opening 212, where the passage 208 extends from the opening 212 along the axial direction A and terminates within the main body 204 at a location proximal to the distal end 200b. However, it is contemplated that in other embodiments the distal end 200b of the main body 204 can be open.

The proximal end 200a of the main body 204 can define a ridge 220 that extends radially outwards from the outer surface 204a of the main body 204. The ridge 220 can extend circumferentially around an entirety of the main body 204, and can define the proximal-most portion of the tamper evident cap 200. However, in other embodiments the ridge 220 can be located elsewhere on the tamper evident cap 200 or extend to different extends about the tamper evident cap 200. The tamper evident cap 200 an also include a plurality of ribs 216 that extend radially outwards from the outer surface 204a of the main body 204 distal to the ridge 220, where the plurality of ribs 216 are positioned circumferentially about the outer surface 204a. The ribs 216 can define substantially hemispherical shapes, and can be spaced apart equidistantly about the circumference of the tamper evident cap 200. However, though one particular number and arrangement of ribs 216 is shown, other numbers and arrangements are contemplated. In operation, the ribs 216 can be configured to engage the film 250 so as to secure the film 250 to the tamper evident cap 200, as will be described further below. Although the tamper evident cap 200 is depicted to have a plurality of ribs 216 extending circumferentially around an entirety of the main body 204, other means for engaging with the film 250 are contemplated, such as alternative types of protrusions, patterns, and/or textures. In some embodiments, the type, pattern, and/or texture of the protrusions can be indicative of the type of material contained within the chamber 109 of the syringe 100. This allows the user of the syringe assembly 10 to easily determine what material is within the syringe 100 and helps avoid incorrect medicaments from being mistakenly applied to a patient.

In the depicted embodiment, the inner surface 204b is substantially smooth. However, in other embodiments, the inner surface 204b is textured or comprises one or more protrusions that extend radially inwards from the inner surface 240b. In one embodiment, the inner surface 204b comprises a plurality of ribs positioned circumferentially about the inner surface 204b that are configured to be positioned between complementary ribs 166 positioned circumferentially about the outer surface of the tip cap 150.

In operation, after the tip cap 150 is engaged with the Luer connection 140, the tamper evident cap 200 can be disposed over the tip cap 150. In some embodiments, when the tamper evident cap 200 is disposed over the tip cap 150, the tamper evident cap 200 is spaced in an entirety from the tip cap 150, the Luer connection 140, and the syringe 100. In other embodiments, when the tamper evident cap 200 is disposed over the tip cap 150, the tamper evident cap 200 is at least partially engaged with the tip cap 150, the Luer connection 140 and/or the syringe 100. For example, when disposed over the tip cap 150, the distal-most portion of the inner surface 204b of the tamper evident cap 200 can contact the distal-most surface of the distal end 150b of the tip cap 150. In other embodiments, the inner surface 204b of the tamper evident cap 200 can be engaged with the outer surface of the tip cap 150 and/or the outer surface of the Luer connection 140 along the axial direction A. Preferably, any contact between the tamper evident cap 200 and the tip cap 150 is such that the fluid seal over the outlet 135 is not compromised by the attachment of the tamper evident cap 200 and/or film 250 to the syringe 100 or by the disengagement of the tamper evident cap 200 from the syringe 100 upon breakage of the frangible connection 254 of the film 250.

In the depicted embodiment, the tamper evident cap 200 may not include any features so as to secure the tamper evident cap 200 to the tip cap 150, the Luer connection 140 and/or the syringe 100. As a result, the tamper evident assembly 180 can include a film 250 disposed over portions of the syringe assembly 10 to secure the tamper evident cap 200 to the Luer connection 140 and/or the syringe 100. The film 250 can define a body that extends from a proximal end 250a to a distal end 250b that is opposite the proximal end 250a along the axial direction A. In the depicted embodiment, the proximal end 250a of the film 250 can be disposed around a portion of the barrel body 103 of the syringe 100, while the distal end 250b of the film 250 can be disposed around a portion of the tamper evident cap 200. A portion of the film 250 between the proximal end 250a and the distal end 250b can also engage the tip cap 150 and/or the outer surface of the Luer connection 140.

In some embodiments, the film 250 is continuous through at least a distal portion of the syringe 100, the entire Luer connection 140, and at least a proximal portion of the tamper evident cap 200. In certain embodiments, the film 250 may extend on the syringe 100 for a length equal or more than 5 mm, e.g., 10 mm, 15 mm, 20 mm, 30 mm, or more, as measured from the distal end 100b of the syringe 100. Alternatively, or additionally, the film 250 may extend onto the syringe 100 for a length equal to or more than 10%, e.g., 20%, 40%, 60%, or more of the length of the syringe barrel body 103. In certain embodiments, the film 250 may extend on the tamper evident cap 200 for a length equal to or more than 2 mm, e.g., 3 mm, 4 mm, 5 mm, 6 mm, or more, as measured from the proximal end 200a. Alternatively, or additionally, the film 250 may extend onto the tamper evident cap 200 for a length equal to or more than 10%, e.g., 20%, 40%, 60%, or more of the length of the tamper evident cap 200. In other embodiments, the film 250 is continuous from at least a proximal portion of the Luer connection 140 to at least a proximal portion of the tamper evident cap 200, but does not cover any portion of the syringe 100. In yet other embodiments, the film 250 is continuous over the entire Luer connection 140 and at least a proximal portion of the tamper evident cap 200, but does not cover any portion of the syringe 100.

In operation, after the tip cap 150 engages the Luer connection 140 and the tamper evident cap 200 is disposed over the tip cap 150, the film 250 can be fitted over the tamper evident cap 200, the Luer connection 140 and/or the syringe 100 so as to secure the tamper evident cap 200 to the Luer connection 140 and/or the syringe 100. In particular, the ribs 216 that extend radially outwards from the outer surface of the tamper evident cap 200 can be configured to secure the distal end 250b of the film 250 to the tamper evident cap 200. Similarly, the ribs 143 that extend radially from the outer surface of the Luer connection 140 can be configured to secure a portion of the film 250 to the Luer connection 140. In one embodiment, the engagement between the film 250 and the tamper evident cap 200, the tip cap 150, the Luer connection 140, and/or the syringe 100 is formed by shrink-wrapping the film 250 over the tamper evident cap 200, the Luer connection 140, and/or the syringe 100. In some embodiments, the tamper evident cap 200 is disposed over the entirety of the Luer connection 140 such that the film 250 is secured to the tamper evident cap 200 and a distal end of the syringe 100, but the film does not directly contact the Luer connection 140. In such embodiments, the tamper evident cap 200 is secured to the Luer connection 140 indirectly, i.e., without any direct contact between the film 250 and the Luer connection 140. Further, the film 250 can be adhesive-bonded to the tamper evident cap 200. Additionally, the film 250 can be adhesive-bonded to the Luer connection 140 and/or the syringe 100. In addition to the above-described methods of attaching the film 250 to the other components of the syringe assembly 10, various other methods of attaching the film 250 may be utilized as desired.

To disengage the tamper evident cap 200 from the tip cap 150 and the syringe 100, the film 250 can include a frangible connection 254 positioned axially between the proximal and distal ends 250a, 250b of the film 250. The frangible connection 254 is configured to be the portion of the syringe assembly 10 that indicates to a user whether the syringe assembly 10 has been tampered with. When the film 250 secures the tamper evident cap 200 to the tip cap 150 and the syringe 100, the frangible connection 254 is configured to break under a force applied to the tamper evident cap 200. This force can be a clockwise or counter-clockwise rotational force, or any other force as desired. When the frangible connection 254 breaks, the tamper evident cap 200 is configured to disengage from the tip cap 150. As a result, the distal end 250b of the film 250 can remain attached to the tamper evident cap 200 and disengage from the remainder of the syringe assembly 10. If a user of the syringe assembly 10 sees that the frangible connection 254 of the film 250 is broken, the user knows that the material within the chamber 109 of the syringe 100 may have been tampered with. However, if the frangible connection 254 is intact, the user can be assured of a greatly reduced risk that the material has been tampered with. Further, breaking the frangible connection 254 can prevent the tamper evident cap 200 from being reattached to the tip cap 150.

As depicted, the frangible connection 254 can comprise a plurality of frangible bridges 258 positioned circumferentially around the body of the film 250. The frangible bridges 258 can be positioned around an entirety of the circumference of the film 250, such that when the frangible connection 254 breaks, the distal end 250b of the film 250 can be completely separated from the proximal end 250a. Each of the frangible bridges 258 can comprise a thin, elongate portion of the film 250 that defines a substantially constant width as they extend along the axial direction A. However, it is contemplated that each of the frangible bridges 258 can taper in width along the axial direction A. Further, the frangible bridges 258 can be equidistantly spaced about the circumference of the film 250, though various other spacing is contemplated. The frangible connection 254 can also define a plurality of gaps 262 that extend through the film 250 from its outer surface to its inner surface. Each of the gaps 262 can extend circumferentially between two adjacent frangible bridges 258. In the depicted embodiment, each of the gaps 262 defines a substantially rectangular shape. Though each of the gaps 262 is shown as having a particular design, each of the gaps 262 can vary in design and spacing along with the design and spacing of each frangible bridge 258. The inclusion of the frangible bridges 258 and gaps 262 allows the film 250 to be easily broken at the frangible connection 254. Though the frangible connection 254 is depicted to comprise a plurality of frangible bridges 258 positioned around an entirety of the circumference of the film, other methods of forming a frangible connection 254 are contemplated, such as tear strips or pull tabs.

The film 250 can be made of a thermoplastic material selected from the group consisting of polyvinyl chloride (PVC), ethylene vinyl acetate (EVA), polyethylene terephthalate (PET), oriented polystyrene (OPS), oriented polypropylene (OPP), polylactic acid (PLA) and mixtures thereof. In certain embodiments, the film 250 is made of PVC. In some embodiments, the interior surface of the film 250 or a portion thereof further comprises an adhesive material, such as a glue or a heat-activated adhesive. In certain embodiments, the interior surface of the distal end 250b of the film 250 to be disposed around a portion of the tamper evident cap 200 comprises an adhesive material.

The film 250 can be blank, or the film 250 can be printed with information relating to the material contained within the chamber 109 of the syringe 100, e.g., active ingredient name, brand name, active ingredient concentration, volume, manufacturer, lot number, etc. The film 250 can be fully transparent, partially transparent, or substantially opaque. The film 250 can also include a color-coded portion 266 that is indicative of the type of material contained within the chamber 109 of the syringe 100. This allows the user of the syringe assembly 10 to easily determine what material is within the syringe 100 and helps avoid incorrect medicaments from being mistakenly applied to a patient. In one embodiment, the color-coded portion 266 comprises a substantially solid band that defines at least a portion of the distal end 250b of the film 250 and extends circumferentially around the film 250. However, alternative placements, shapes, and sizes of the color-coded portion 266 are contemplated. The color of the color-coded portion 266 can be selected from a plurality of colors that each correspond to a different material. In one embodiment, the relationship between the color of the color-coded portion 266 and the material contained within the syringe 100 can conform to the labeling standards set by ASTM D4774, such that the color-coded portion 266 can be universally recognized and understood within any variety of medical environments. The standards set by ASTM D4774 are shown in the below table. The examples provided for each drug class are exemplary only and not meant to be exhaustive. Drugs that do not fit into the classes shown in Table 1 can be labeled with black printing on a white background according to ASTM D4774 standards. Exceptions are noted by the "A" superscript.

TABLE 1

ASTM D4774 Standards

| Drug Class | Examples | Pantone Color |
| --- | --- | --- |
| Induction Agents | Etomidate, Ketamine, Methohexital, Propofol. Thiamylal, Thiopental | Yellow |
| Benzodiazepines | Diazepam, Midazolam | Orange 151 |
| Benodiazepine Receptor Antagonist | Flumazenil | Orange 151 and White Diagonal Stripes |
| Muscle Relaxants (Depolarizer) | Succinylcholine[A] | Fluorescent Red 805 |
| Muscle Relaxants (Non Depolarizer) | Atracurium, Cisatracurium, Mivacurium. Pancuronium, Rocuronium, Vecuronium | Fluorescent Red 805 |
| Relaxant Antagonist (Non-Depolarizer) | Endophonium, Neostigmine, Pyridostigmine | Fluorescent Red 805 and White Diagonal Stripes |
| Narcotics | Alfentanil, Fentanyl, Hydromorphone, Meperidine, Morphine, Sufentanil, Remifentanil | Blue 297 |
| Narcotic Antagonists | Levallorphan, Naloxone | Blue 297 and White Diagonal Stripes |
| Vasopressors | Ephedrine, Norepinephrine, Phenylephrine. Epinephrine[A] | Violet 256 |
| Hypotensive Agents | Hydralazine, Nitroglycerine, Nitroprusside, Phentolamine, Trimethaphan | Violet 256 and White Diagonal Stripes |
| Local Anesthetics | Bupivacaine, Chloroprocaine, Lidocaine, Mepivacaine, Procaine, Ropivacaine, Tetracaine | Gray 401 |
| Anticholinergic Agents | Atropine, Glycopyrrolate, Scopolamine | Green 367 |
| Beta Blockers | Esmolol, Labetolol, Metroprolol | White Background with Copper 876U Bar Across Drug Name |
| Major Tranquilizers and Anti-Emetics | Droperidol, Inapsine, Haloperidol, Levomepromazine, Metoclopramide, Ondasetron | Salmon 156 |

[A]Printed against the background color as reversed plate letters with a black bar running from edge to edge of the film Though the film 250 is described as including a color-coded portion 266, it is also contemplated that in other embodiments all or a portion of the main body 204 of the tamper evident cap 200 defines a color-coded portion that is indicative of the type of material within the chamber 109 of the syringe 100 in combination with or in place of the color-coded portion 266. This can be done through molding the color-coded portion of the tamper evident cap 200 out of a material having the color that corresponds to the type of the material. Like the color-coded portion 266, the color-coded portion of the tamper evident cap 200 can comprise a color selected from a plurality of colors that each correspond to a different material. In one embodiment, the color-coded portion of the tamper evident cap 200 can conform to the labeling standards set by ASTM D4774.

Another embodiment of the present disclosure is a pharmaceutical product comprising a syringe assembly 10 and a secondary packaging system therefor. In some embodiments, the secondary packaging is a pouch, blister, flow wrapper, or bag. The secondary packaging can be comprised of an oxygen, light, and/or moisture barrier material, such as high-density polyethylene (HDPE), ethylene/vinyl alcohol copolymer (EVOH), polypropylene (PP), polyethylene terephthalate (PET), polyethylene naphthalate (PEN), and polyamide (PA), metalized film, aluminum foil, oxide coated films, and combinations thereof. In certain embodiments, the secondary packaging system also comprises an oxygen absorber. The oxygen absorber can be a sachet, pouch, canister, capsule, sticker, or strip that is placed inside of the secondary packaging. Alternatively, or additionally, the oxygen absorber can be incorporated into the material of the secondary packaging. In some embodiments, the oxygen absorber is selected from the group consisting of reduced iron compounds, catechol, ascorbic acid and analogs thereof, metal ligands, unsaturated hydrocarbons and polyamides.

Yet another embodiment of the present disclosure is a pharmaceutical product comprising a plurality of syringe assemblies 10 and a container therefor. In some embodiments, the container is a box, carton, case, package, tray, or tin. Optionally, one or more of the syringe assemblies 10 can be enclosed within a secondary packaging system before being placed into the container. In certain embodiments, each syringe assembly 10 enclosed within the container is filled with the same active ingredient. In other embodiments, each syringe assembly 10 enclosed within the container is filled with a different active ingredient from the same drug class, a different active ingredient from a different drug class, or any combination thereof. For example, the pharmaceutical product can comprise a plurality of syringe assemblies 10 enclosed with a container, wherein the two or more of the syringe assemblies 10 are filled with a different active ingredient from a first drug class, and one or more syringe assemblies 10 are filled with an active ingredient from a second drug class.

Figure 5:
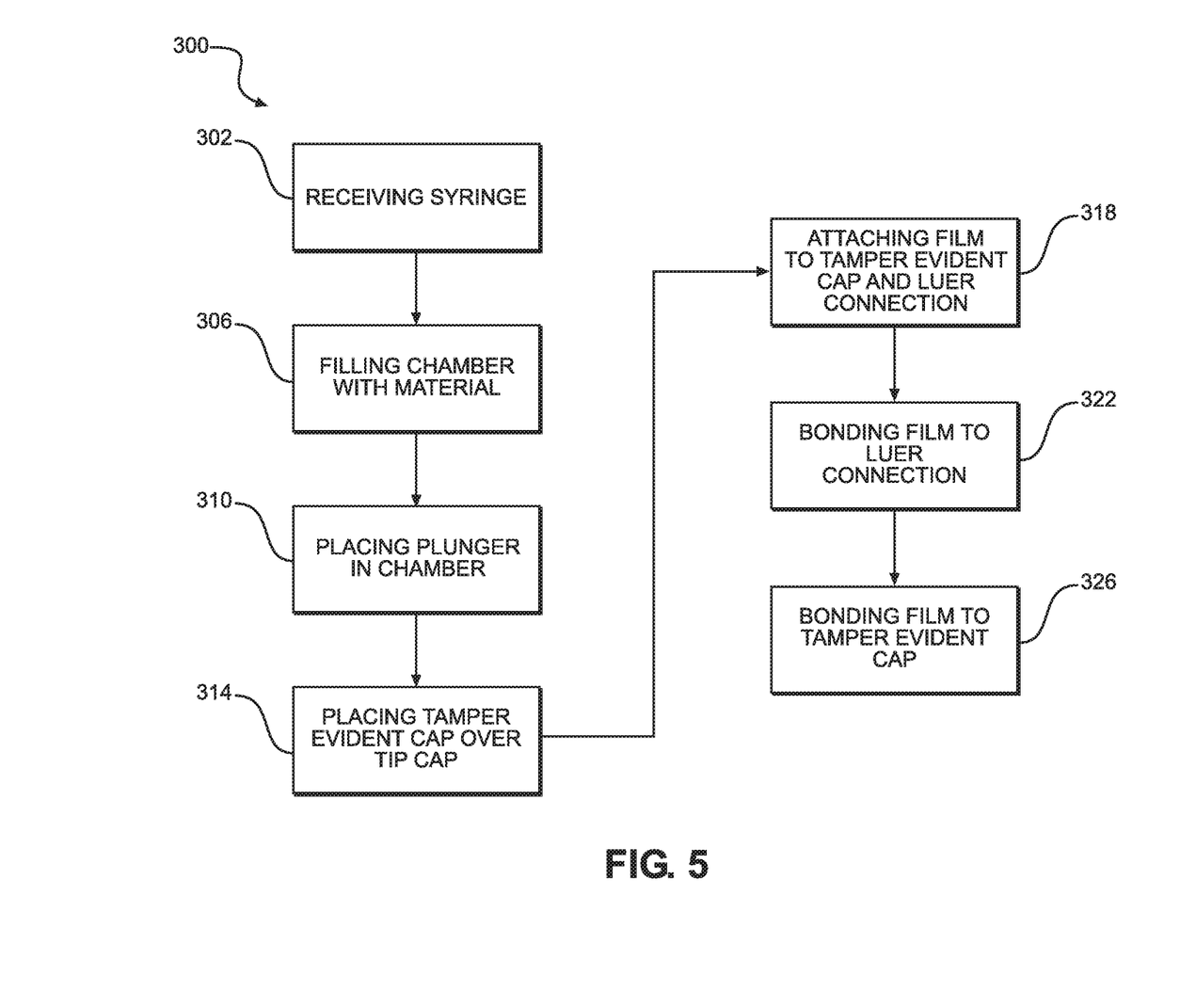
FIG. 5 illustrates a process flow diagram of a method of filling a syringe with a material according to an embodiment of the present disclosure.

Now referring to FIG. 5, a method 300 of filling the syringe 100 will be described. Method 300 begins with step 302, which comprises receiving the syringe 100, where the syringe 100 comprises the barrel body 103 extending from a distal end 100b having a Luer connection 140 and a tip 126 to an open proximal end 100a. As stated above, the barrel body 103 defines a chamber 109 that extends along the axial direction A therethrough. Further, the tip 126 is configured to be received within the central passage 154 of the tip cap 150, such that the inner surface of the tip cap 150 creates a fluid seal over the tip 126 and the outlet 135. Then, step 306 comprises filling the chamber 109 with the material through the proximal end 100a of the syringe 100. Next, in step 310, the plunger 50, which is connected to the plunger rod 25, is disposed within the chamber 109.

After step 310, step 314 involves placing the tamper evident cap 200 over the tip cap 150. In an alternative embodiment, step 314 can be performed after the syringe 100 and tip cap 150 are received and before the chamber 109 is filled with material. As stated above, though the distal-most portion of the inner surface of the tamper evident cap 200 may contact the distal-most portion of the outer surface of the tip cap 150 when the tamper evident cap 200 is placed over the tip cap 150, the contact between the tamper evident cap 200 and the tip cap 150 may not be sufficient to secure the tamper evident cap 200 to the tip cap 150. Accordingly, in step 318 the film 250 can be attached to the tamper evident cap 200 and the Luer connection 140 such that the film 250 secures the tamper evident cap 200 to the Luer connection 140. In step 318, the film 250 can also be attached to the syringe 100. As stated previously, the tamper evident cap 200 can include ribs 216 that promote a stronger engagement between the tamper evident cap 200 and the film 250, and the Luer connection 140 can include ribs 143 that promote a stronger engagement between the Luer connection 140 and the film 250. As a result, the film 250 can secure the tamper evident cap 200 to the Luer connection 140 and the syringe 100 until the frangible connection 254 of the film 250 is broken under a force applied to the tamper evident cap 200, at which time the tamper evident cap 200 can disengage from the tip cap 150.

In one embodiment, step 318 includes shrink-wrapping the film 250 over the tamper evident cap 200 and the Luer connection 140. However, other methods of attaching the film 250 to the tamper evident cap 200 and the Luer connection 140 are contemplated. To create a more secure engagement between the film 250 and the Luer connection 140, method 300 can include step 322, which involves bonding the film 250 to the Luer connection 140 and/or the syringe 100 via an adhesive. Additionally, to create a more secure engagement between the film 250 and the tamper evident cap 200, method 300 can include step 326, which involves bonding the film 250 to the tamper evident cap 200 via an adhesive. However, both of steps 322 and 326 are optional, as they can be each be performed in isolation, in conjunction with each other, or not at all. As stated above, the film 250 can also include a color-coded portion 266 that is indicative of the type of material contained within the chamber 109 of the syringe 100. The color of the color-coded portion 266 can be selected from a plurality of colors that each correspond to a different material. In one embodiment, the relationship between the color of the color-coded portion 266 and the material contained within the syringe 100 can conform to the labeling standards set by ASTM D4774, such that the color-coded portion 266 can be universally recognized and understood within any variety of medical environments.

Figure 6:
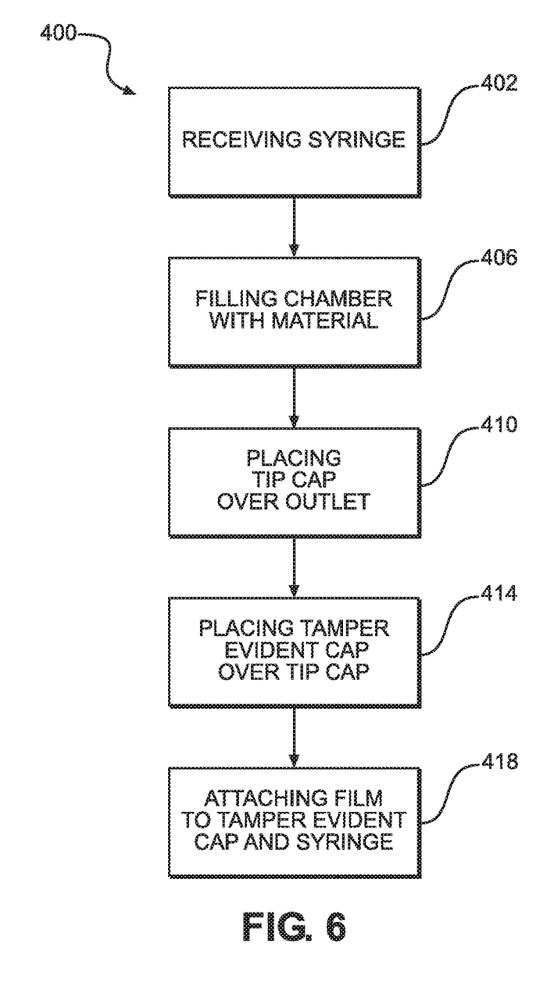
FIG. 6 illustrates a process flow diagram of a method of filling a syringe with a material according to another embodiment of the present disclosure.

In another embodiment, as shown in FIG. 6, a method 400 of filling the syringe 100 with a material begins with step 402, which comprises receiving the syringe 100. Then, step 406 comprises filling the chamber 109 of the syringe 100 with the material through the outlet 135 of the tip 126. After step 406, in step 410 the tip cap 150 is placed over outlet 135 of the tip 126 to create a fluid seal over the outlet 135. Next, in step 414, the tamper evident cap 200 is placed over the tip cap 150. To secure the tamper evident cap 200 to the tip cap 150, in step 418 the film 250 is attached to the tamper evident cap 200 and the syringe 100 as described above in the context of method 300.

Figure 7:
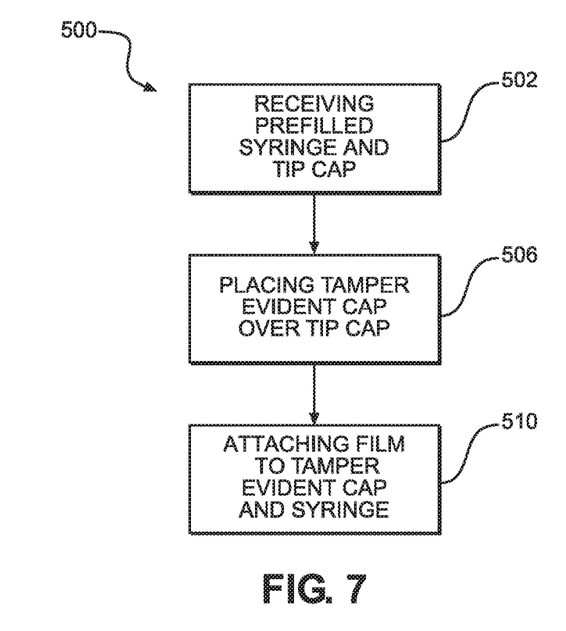
FIG. 7 illustrates a process flow diagram of a method of applying a tamper evident cap and film to a prefilled syringe according to an embodiment of the present disclosure.

In yet another embodiment of the invention, as shown in FIG. 7, a method 500 of applying the tamper evident cap 200 to the syringe 100, which is prefilled, is shown. Method 500 begins with step 502, in which the syringe 100 is received prefilled with a material and the tip cap 150 is already placed over the outlet 135 of the tip 126. Then, the tamper evident cap 200 is placed over the tip cap 150 in step 506. To secure the tamper evident cap 200 to the tip cap 150, in step 510 the film 250 is attached to the tamper evident cap 200 and the syringe 100 as described above in the context of method 300.

The material contained within the chamber 109 of the syringe 100 in the syringe assemblies 10 typically is a liquid, which can be aqueous, non-aqueous, or a combination of aqueous and non-aqueous liquids. In some embodiments, the liquid is a diluent intended for mixing with an active ingredient prior to administration to a subject. Exemplary diluents include, but are not limited to, water, 0.9% saline, 5% dextrose, Ringer's lactate solution, and other pharmaceutically acceptable diluents. In other embodiments, the liquid is a pharmaceutical formulation comprising an active ingredient and, optionally, one or more excipients. Thus, the invention provides a pharmaceutical product comprising a syringe assembly according to the present invention, wherein the liquid is a pharmaceutical formulation. Suitable excipients include, but are not limited to, a tonicity modifier, antioxidant, buffer, pH adjuster, preservative, solubilizer, stabilizer, or a combination of any of the forgoing. A diluent or pharmaceutical formulation can take on any suitable physical form including, but not limited to, solution, suspension, emulsion, or dispersion.

The active ingredient of the pharmaceutical formulation can be a therapeutic agent, a diagnostic agent, a nutrient, or a combination thereof. Examples of therapeutic agents include, but are not limited to antiinfectives, anesthetics, analgesics, anticoagulants, chemotherapeutics, hormones, antihypertensives, antiinflammatories, antiemetics, bronchodilators, adrenergics, immunoglobulins, antipsychotics, antidepressants, and combinations thereof. Examples of diagnostic agents include, but are not limited to x-ray, MRI and ultrasound contrast agents, cholecystokinetics, vasodilators, and combinations thereof. Examples of nutrients include, but are not limited to, salts, carbohydrates, minerals, vitamins, lipids, and combinations thereof.

In some embodiments, the active ingredient is a compound useful for pain management, muscle relaxation, sedation, and/or anesthesia. In certain embodiments, the active ingredient is an opioid, a benzodiazepine, a beta blocker, or an $\alpha_2$-adrenergic receptor agonist. In particular embodiments, the active ingredient is morphine, hydromorphone, hydrocodone, oxycodone, oxymorphone, codeine, buprenorphine, naloxone, naltrexone, fentanyl, remifentanil, sufentanil, alfentanil, meperidine, rocuronium, vecuronium, midazolam, lorazepam, diazepam, neostigmine, atropine, glycopyrrolate, dexmedetomidine, cisastracurium, ropivacaine, lidocaine, propofol, ketamine, succinylcholine, or a combination of the foregoing.

In other embodiments, the active ingredient is moxifloxacin, linezolid, levofloxacin, levetiracetam, vancomycin, cefepime, aztreonam, cefoxitin, ceftriaxone, cefazolin, cefotaxime, ceftazidime, gentamicin, oxacillin, nafcillin, penicillin, cefuroxime, ticarcillin, clavulanic acid, piperacillin, tazobactam, azithromycin, meropenem, ertapenem, tigecycline, micafungin, metronidazole, fluconazole, itraconazole, posaconazole, heparin, enoxaparin, dalteparin, theophylline, acetaminophen (paracetamol), ibuprofen, acetylcysteine, decitabine, azacitidine, docetaxel, pemetrexed, palonosetron, aprepitant, fosaprepitant, famotidine, amiodarone, nitroglycerin, nicardipine, clevidipine, dobutamine, esmolol, labetalol, metroprolol, somatropin, liraglutide, abaloparatide, semaglutide, teriparatide, degarelix, sumatriptan, epinephrine, ephedrine, vasopressin, methotrexate, testosterone, hydroxyprogesterone, or a combination of the foregoing.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts, and features of the inventions—such as alternative materials, structures, configurations, methods, devices and components, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features, and concepts may be expressly identified herein as being inventive or forming part of an invention, such identification is not intended to be exclusive, but rather there may be inventive aspects, concepts, and features that are fully described herein without being expressly identified as such or as part of a specific invention, the scope of the inventions instead being set forth in the appended claims or the claims of related or continuing applications. Descriptions of exemplary methods or processes are not limited to inclusion of all steps as being required in all cases, nor is the order that the steps are presented to be construed as required or necessary unless expressly so stated.

While the invention is described herein using a limited number of embodiments, these specific embodiments are not intended to limit the scope of the invention as otherwise described and claimed herein. The precise arrangement of various elements and order of the steps of articles and methods described herein are not to be considered limiting. For instance, although the steps of the methods are described with reference to sequential series of reference signs and progression of the blocks in the figures, the method can be implemented in a particular order as desired.

What is claimed is:

1. A syringe assembly, comprising:
    a syringe having a barrel body that extends from a proximal end to a distal end and defines a chamber extending along an axial direction therethrough, a luer connection at the distal end, and a tip extending from the distal end along the axial direction and defining an outlet in fluid communication with the chamber, wherein the chamber contains a material;
    a plunger received within the chamber of the syringe to create a fluid seal within the barrel body;
    a tip cap defining a central passage configured to receive a portion of the tip such that the tip cap creates a fluid seal over the outlet;
    a tamper evident assembly, comprising:
        a tamper evident cap disposed over the tip cap, wherein the tamper evident cap has a main body that defines a proximal end defining an opening, a closed distal end opposite the proximal end along the axial direction, an outer surface, and an inner surface opposite the outer surface that defines a passage extending from the opening of the proximal end configured to receive the tip cap; and
        a film including a frangible connection and configured to secure the tamper evident cap to the luer connection,
    wherein the frangible connection is configured to break under a force applied to the tamper evident cap such that the tamper evident cap is configured to disengage from the luer connection when the frangible connection breaks.

2. The syringe assembly of claim 1, wherein the film is shrink-wrapped over a portion of the tamper evident cap and at least a portion of the luer connection.

3. The syringe assembly of claim 1, wherein the film includes a color-coded portion that comprises a color selected from a plurality of colors that each correspond to a different material.

4. The syringe assembly of claim 3, wherein the color of the color-coded portion corresponds to the material in accordance with ASTM D4774.

5. The syringe assembly of claim 1, wherein the film is adhesive-bonded to the tamper evident cap.

6. The syringe assembly of claim 1, wherein the film is adhesive-bonded to the luer connection.

7. The syringe assembly of claim 1, wherein the tamper evident cap includes a plurality of ribs extending radially outwards from the outer surface and configured to secure the film to the tamper evident cap.

8. The syringe assembly of claim 1, wherein the film is configured to engage the distal end of the syringe.

9. The syringe assembly of claim 1, wherein the luer connection includes a plurality of ribs extending outwards from an outer surface and configured to secure the film to the luer connection.

10. The syringe assembly of claim 1, wherein a portion of the main body defines a color-coded portion that comprises a color selected from a plurality of colors that each correspond to a different material.

11. The syringe assembly of claim 1, wherein the tamper evident cap is spaced in an entirety from the syringe when the tamper evident cap engages the tip cap.

12. The syringe assembly of claim 1, wherein a portion of the tamper evident cap is in contact with the tip cap.

13. The syringe assembly of claim 12, wherein the fluid seal over the outlet is not compromised when the tamper evident cap is in contact with the tip cap or when the frangible connection is broken.

14. The syringe assembly of claim 1, wherein the material includes an active ingredient that is (a) a therapeutic agent selected from a group consisting of anti-infectives, anesthetics, analgesics, anticoagulants, chemotherapeutics, hormones, antihypertensives, anti-inflammatories, antiemetics, bronchodilators, adrenergics, immunoglobulins, antipsychotics, and antidepressants or (b) a diagnostic agent selected from a group consisting of x-ray, MRI and ultrasound contrast agents, cholecystokinetics, and vasodilators.

15. The syringe assembly of claim 1, wherein the material includes an active ingredient selected from a group consisting of an opioid, benzodiazepine, α2-adrenergic receptor agonist, beta blocker, morphine, hydromorphone, hydrocodone, oxycodone, oxymorphone, codeine, buprenorphine, naloxone, naltrexone, fentanyl, remifentanil, sufentanil, alfentanil, meperidine, rocuronium, vecuronium, midazolam, lorazepam, diazepam, neostigmine, atropine, glycopyrrolate, dexmedetomidine, cisastracurium, ropivacaine, lidocaine, propofol, ketamine, succinylcholine, moxifloxacin, linezolid, levofloxacin, levetiracetam, vancomycin, cefepime, aztreonam, cefoxitin, ceftriaxone, cefazolin, cefotaxime, ceftazidime, gentamicin, oxacillin, nafcillin, penicillin, cefuroxime, ticarcillin, clavulanic acid, piperacillin, tazobactam, azithromycin, meropenem, ertapenem, tigecycline, micafungin, metronidazole, fluconazole, itraconazole, posaconazole, heparin, enoxaparin, dalteparin, theophylline, acetaminophen (paracetamol), ibuprofen, acetylcysteine, decitabine, azacitidine, docetaxel, pemetrexed, palonosetron, aprepitant, fosaprepitant, famotidine, amiodarone, nitroglycerin, nicardipine, clevidipine, dobutamine, esmolol, labetalol, metroprolol, somatropin, liraglutide, abaloparatide, semaglutide, teriparatide, degarelix, sumatriptan, epinephrine, ephedrine, vasopressin, methotrexate, testosterone, and hydroxyprogesterone.

16. A method of filling a syringe with a material, the method comprising:
  receiving a syringe having a barrel body extending from a distal end having a luer connection and a tip, wherein the tip defines an outlet having a tip cap placed thereon, to an open proximal end, the barrel body defining a chamber that extends along an axial direction therethrough;
  filling the chamber with the material through the open proximal end;
  placing a plunger at the open proximal end of the chamber;
  placing, after placing the plunger at the open proximal end of the chamber, a tamper evident cap over the tip cap; and
  attaching a film to the tamper evident cap and the luer connection such that the film secures the tamper evident cap to the luer connection.

17. The method of claim 16, wherein attaching the film includes shrink-wrapping the film over the tamper evident cap and the luer connection.

18. The method of claim 16, wherein attaching the film includes attaching the film to the syringe.

19. The method of claim 16, wherein the film includes a color-coded portion that comprises a color selected from a plurality of colors that each correspond to a different material.

20. The method of claim 19, wherein the color of the color-coded portion corresponds to the material in accordance with ASTM D4774.

21. The method of claim 16, further comprising:
  bonding the film to the luer connection via an adhesive.

22. The method of claim 16, further comprising:
  bonding the film to the tamper evident cap via an adhesive.

23. The method of claim 16, wherein the film includes a frangible connection configured to break under a force applied to the tamper evident cap such that the tamper evident cap is configured to disengage from the luer connection when the frangible connection breaks.

24. A tamper evident assembly, comprising:
  a tamper evident cap having a main body that defines a proximal end defining an opening, a closed distal end opposite the proximal end along an axial direction, an outer surface, and an inner surface opposite the outer surface that defines a passage extending from the opening of the proximal end configured to receive a tip cap and a luer connection of a syringe; and
  a film including a frangible connection and configured to secure the tamper evident cap to the luer connection, wherein the frangible connection is configured to break under a force applied to the tamper evident cap such that the tamper evident cap is configured to disengage from the luer connection when the frangible connection breaks.

25. The tamper evident assembly of claim 24, wherein the frangible connection extends circumferentially around the tamper evident cap.

* * * * *